United States Patent
Sanders (10) Patent No.: US 7,483,144 B2
(45) Date of Patent: Jan. 27, 2009

(54) APPARATUS AND METHOD FOR RESONANT CHEMICAL AND BIOLOGICAL SENSING

(75) Inventor: Glen A. Sanders, Scottsdale, AZ (US)

(73) Assignee: Honeywell International, Inc., Morristown, NJ (US)

( * ) Notice: Subject to any disclaimer, the term of this patent is extended or adjusted under 35 U.S.C. 154(b) by 144 days.

(21) Appl. No.: 11/713,237

(22) Filed: Mar. 2, 2007

(65) Prior Publication Data

US 2008/0212104 A1    Sep. 4, 2008

(51) Int. Cl.
  *G01B 9/02*    (2006.01)
  *G02B 6/00*    (2006.01)
  *G01N 21/00*    (2006.01)
  *G01N 21/03*    (2006.01)

(52) U.S. Cl. ............... 356/480; 385/12; 422/82.11; 436/165

(58) Field of Classification Search ............... 356/480, 356/517, 451; 385/12; 422/82.08, 82.11; 436/165, 171, 801
See application file for complete search history.

(56) References Cited

U.S. PATENT DOCUMENTS

| | | | |
|---|---|---|---|
| 4,834,496 A | | 5/1989 | Blyler, Jr. et al. |
| 5,009,505 A | * | 4/1991 | Malvern ............ 356/480 |
| 6,205,263 B1 | | 3/2001 | Lieberman et al. |
| 7,327,460 B2 | * | 2/2008 | Sanders et al. ........ 356/461 |
| 7,372,574 B2 | * | 5/2008 | Sanders et al. ........ 356/461 |
| 7,388,671 B2 | * | 6/2008 | Sanders et al. ........ 356/461 |
| 2003/0109055 A1 | * | 6/2003 | Lehmann et al. ........ 436/164 |
| 2006/0227331 A1 | * | 10/2006 | Vollmer et al. ........ 356/483 |
| 2007/0086015 A1 | * | 4/2007 | Sanders et al. ........ 356/461 |
| 2007/0097375 A1 | * | 5/2007 | Sanders et al. ........ 356/461 |
| 2007/0133003 A1 | * | 6/2007 | Sanders et al. ........ 356/461 |

(Continued)

FOREIGN PATENT DOCUMENTS

EP    1213583    6/2002

(Continued)

OTHER PUBLICATIONS

Soan Kim et al. "A Dual-Concentric-Core Photonic Crystal Fiber for Broadband Dispersion Compensation." Journal of the Korean Physical Society, Seoul, KR, vol. 49, No. 4, Oct. 1, 2006, pp. 1434-1437.

*Primary Examiner*—Patrick J Connolly
(74) *Attorney, Agent, or Firm*—P. G. Scott Born; Black Lowe & Graham PLLC (57) ABSTRACT

Apparatus and method are provided for chemical and biological agent sensing. The sensing apparatus includes a resonator having a resonance frequency. The resonator includes a coil of a photonic crystal fiber. The photonic crystal fiber has a solid region configured to guide a substantially single optical mode of light having an evanescent tail, a first cladding surrounding an exterior of the solid region, and a polymer coating the first cladding. The polymer has an embedded indicator. The first cladding and polymer are together configured to extend a portion of the evanescent tail into the polymer. The resonator is configured to produce a resonance shape centered at the resonance frequency. A predetermined change in the resonance shape or the free spectral range indicates a reaction of the indicator to the agent.

20 Claims, 3 Drawing Sheets

U.S. PATENT DOCUMENTS

| | | | |
|---|---|---|---|
| 2007/0201030 A1* | 8/2007 | Sanders | 356/460 |
| 2007/0242276 A1* | 10/2007 | Hughes et al. | 356/461 |
| 2008/0079947 A1* | 4/2008 | Sanders et al. | 356/461 |
| 2008/0137091 A1* | 6/2008 | Sanders et al. | 356/461 |

FOREIGN PATENT DOCUMENTS

| | | |
|---|---|---|
| EP | 1923693 | 5/2008 |

\* cited by examiner

APPARATUS AND METHOD FOR RESONANT CHEMICAL AND BIOLOGICAL SENSING

FIELD OF THE INVENTION

The present invention generally relates to environment sensing, and more particularly relates to optical-based apparatus and methods for detecting the presence of a specific molecule.

BACKGROUND OF THE INVENTION

In recent times, greater emphasis has been placed on national home security and detecting threats to populations. In particular, detecting or sensing the presence of undesired chemicals or biological material in the environment has become a priority, and a variety of detection devices have been developed in response thereto. One possible implementation of a chemical sensor is a sensor using a multi-mode optical fiber having a glass core and a cladding surrounding the core. The cladding, or a coating on the cladding, has optical properties which are altered in the presence of a pre-determined material to be detected. As light is transmitted through the core of the optical fiber, the optical properties of the light vary with respect to changes in optical properties of the cladding or coating interacting with the material to be detected. Some advantages of multi-mode fiber are that the core has a diameter with sufficient structural integrity and can be coated with a chemically sensitive polymer. Some of the core-guided light can interact with this polymer.

Resonators have been implemented in chemical sensors to circulate light around an optical fiber loop for multiple passes. A periodic series of resonance lineshapes is produced, each having a peak centered about a resonance frequency under normal conditions, and the resonance lineshape has a finesse associated therewith. The frequency-periodicity of frequency separation between resonance frequencies of the same mode is the free spectral range of the resonator. As used herein, the term "finesse" refers to a relationship (e.g., sharpness) based on a ratio of the free-spectral range to the linewidth of an individual resonance lineshape. The linewidth of the resonance lineshape is a frequency width at half of the maximum peak value of the resonance lineshape. The finesse additionally relates to the number of times the light recirculates within the optical loop with reproducibility, and thus is inherently related to the round-trip loss of the resonator. Higher losses generally result in lower finesses. It is generally difficult to couple light into a multi-mode optical fiber and maintain the light in a single spatial mode that reproduces itself for multiple circulations through the resonator. For example, perturbations (e.g., imperfections, geometrical distortions, etc.) along the length of the optical fiber typically decrease the round-trip reproducibility of the single fiber spatial mode within a multi-mode fiber, and thus decrease the finesse. Other spatial mode resonances can also be excited which typically cause errors in the intended measurement. In the latter case, a complex structure of resonances, which may be based on a single stable resonance, may be observed that create instabilities and errors in the measurement. Each spatial mode may be associated with two polarization modes, which doubles the number of resonances in the spectrum.

A single mode optical fiber may be used to significantly improve the resonance characteristics of the resonator by assuring that a single spatial mode of the fiber supports the resonance mode of the resonator. For example, this single spatial mode is the sole resonating mode provided that one polarization state is resonating within the resonator. Instabilities created by power sharing between several spatial modes of the fiber and errors resulting from the presence of several resonator modes are thus substantially eliminated. Measurements of the finesse, the linewidth of the resonance, and the free spectral range are typically unique since these relate to the loss and pathlength for light traveling within a single spatial mode of the fiber and for a single resonance lineshape. To make a chemically sensitive fiber, the light should interact with the polymer. Placing a permeable, chemically sensitive polymer cladding directly on the core of a typical single mode fiber is generally impractical because the core is too small (e.g., about 5-10 μm). Such a small glass diameter typically lacks the mechanical strength normally associated with larger chemically sensitive multi-mode optical fibers. Applying a relatively pliable cladding or coating around the core of a single mode optical fiber is also difficult in practice. Adding an intermediate glass cladding between the core and a polymer coating would tend to interfere with sensing.

Accordingly, it is desirable to provide a resonator-based sensor for detecting the presence of chemical and/or biological agents having a high finesse and a stable resonance structure corresponding with the light traveling within a single spatial mode of the fiber. In addition, it is desirable to provide a resonator-based sensor for detecting the presence of chemical and/or biological agents using a single-mode fiber. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

Apparatus and method are provided for sensing one or more agents in an environment. In one exemplary embodiment, an apparatus for sensing an agent in an environment is provided comprising a resonator having a resonance frequency and comprising a coil. The coil comprises a photonic crystal fiber. The photonic crystal fiber comprises a solid region configured to guide a substantially single optical mode of light, a first cladding surrounding an exterior of the solid region, and a polymer coating the first cladding. The substantially single optical mode has an evanescent tail. The polymer is at least partially porous and has an embedded indicator. The first cladding and polymer are together configured to extend a portion of the evanescent tail into the first cladding and the polymer. The resonator is configured to produce a resonance shape centered at the resonance frequency, and a predetermined change in the resonance shape indicates a reaction of the indicator to the agent.

In another exemplary embodiment, an apparatus for sensing an agent in an environment is provided comprising a tunable light source and a resonator having a resonance frequency and comprising a coil. The tunable light source provides an input light. The coil comprises a photonic crystal fiber. The photonic crystal fiber comprises a solid region configured to guide a substantially single optical mode of light, a first cladding surrounding the solid region, and a polymer coating the first cladding. The substantially single optical mode has an evanescent tail. The polymer coating is at least partially porous, and the first cladding comprises a photonic crystalline structure. The polymer has an embedded indicator, and the first cladding and polymer are together configured to extend a portion of the evanescent tail into the first cladding and the polymer. The resonator produces a resonance shape centered at the resonance frequency as the tunable light source is tuned through a region about the resonance frequency, and a predetermined change in the resonance shape or a free spectral range indicates a reaction of the indicator to the agent.

In another exemplary embodiment, a method for sensing an agent in an environment is provided comprising propagating a light wave in a single optical mode through a photonic crystal fiber coil, producing a resonance shape from the single optical mode in which the light wave is circulating through the photonic crystal fiber coil, and detecting a predetermined change in the resonance shape. The photonic crystal fiber coil has a coating and an indicator incorporated in the coating configured to react with the agent. The predetermined change indicates a presence of the first agent in the environment.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Apparatus and method are provided for sensing one or more chemical/biological agents in an environment. In general, the apparatus comprises a resonator having an optical fiber coil of photonic crystal fiber. The fiber is capable of guiding a substantially single optical mode of light that is spatially large (e.g., from about seven (7) to about thirty (30) times the wavelength of light supplied to the resonator) and includes, but is not necessarily limited to, a solid region for guiding the substantially single optical mode of light, a cladding with a photonic crystalline structure (e.g., a periodic hole structure) surrounding the solid region, and a polymer coating the cladding. The fiber may also be configured to guide a single polarization mode. The polymer is at least semi-permeable (e.g., at least partially porous) to a desired agent to be detected, and has an indicator embedded therein to react to such agent.

When an input light beam (e.g., from a light source) is supplied to the resonator and the input light beam is tuned through the region of the resonance frequency of the resonator in one direction (e.g., a clockwise or a counter-clockwise direction of the optical fiber coil in the case of a ring resonator), a resonance lineshape is produced in the region of the resonance frequency, which is sensed by the light circulating through the resonator. Absent the agent to be detected from the environment, the resonance lineshape has a narrow profile, corresponding to a low round-trip energy loss of the light circulating in the resonator. Additionally, using the photonic crystal fiber, which supports a single spatial mode of propagation, increases the stability of the resonance structure and removes other resonance lineshapes that are typically associated with multi-mode fibers, thereby providing an opportunity for accurate lineshape measurements in a resonator with a stable, high finesse lineshape.

With the chemical/biological agent present in the environment of the optical fiber coil, the indicator reacts with the agent and, as a result, a portion of the light circulating in the optical fiber coil is scattered or absorbed. The normally narrow, resonance lineshape changes to a wider, shallower profile. This change in resonance lineshape represents a greater energy loss resulting from the scattered light or absorbed light and thus, indicates the presence of the chemical/biological agent.

Figure 1:
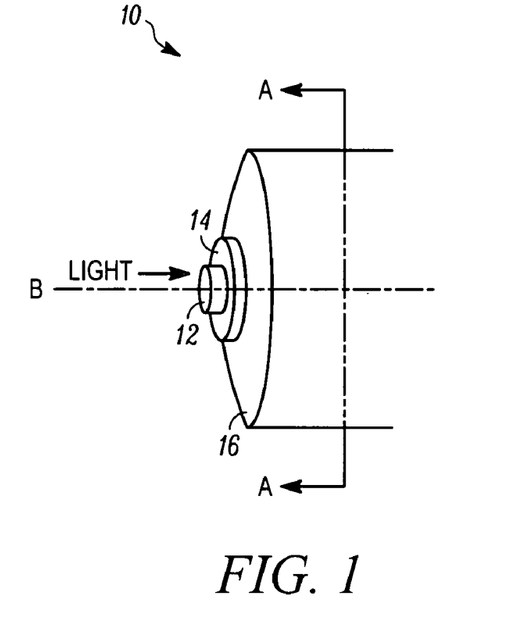
FIG. 1 is a perspective view of a photonic crystal fiber in accordance with an exemplary embodiment.
Figure 2:
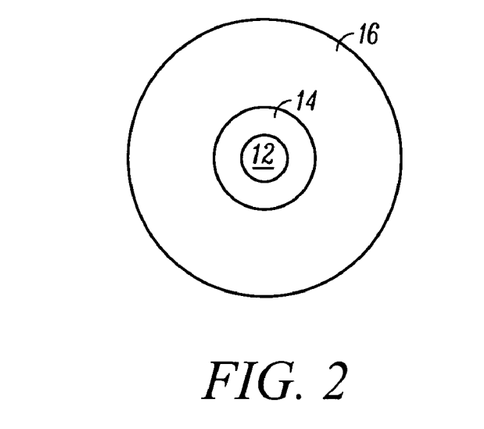
FIG. 2 is a cross-sectional view of the photonic crystal fiber shown in FIG. 1 taken along line A-A.

Referring now to the drawings, FIG. 1 is a perspective view of a large mode (e.g., about ten times (10×) the size of the mode field of conventional single mode fibers), single mode, photonic crystal fiber 10 for chemical sensing in accordance with an exemplary embodiment. FIG. 2 is a cross-sectional view of the fiber 10 shown in FIG. 1 taken along line A-A. The fiber 10 comprises a glass or silica-based core 12, an at least partially porous (e.g., embedded pores) cladding 14 surrounding the core 12, and a polymer 16 having a pre-determined index coated around the cladding 14. The fiber 10 is structured to guide a single optical mode of light, and this optical mode is spatially large. The polymer 16 may be selected to have a lower refractive index than the refractive index of the cladding 14, and the cladding thickness may be selected such that a fraction of an evanescent tail of a light mode traversing through the core 12 extends through the cladding 14 and into the polymer 16.

In some conventional single mode fibers, a solid glass core is surrounded by a cladding that is typically thicker than the cladding 14, and the cladding of conventional single mode fibers is typically surrounded by a plastic coating. However, these conventional single mode fibers are generally ineffective for chemical sensing because the structure is not configured to extend the mode (of the light propagating through the fiber) throughout the cladding and into the plastic jacket.

The mode of the fiber 10 has a diameter that is greater than conventional single mode optical fibers (e.g., greater than 20 µm). Because the diameter of the fiber 10 is significantly greater than the core size of a conventional fiber, the fiber 10 has greater strength than the strength normally associated with conventional single mode optical fibers. The cladding 14 provides additional structural strength, and the dimensions thereof may be engineered such that the cladding 14 has a minimal thickness for maximum light exposure to the polymer 16. The polymer 16 is at least semi-permeable to a predetermined agent and has an indicator embedded therein that reacts to the agent. In another embodiment, the polymer 16 is omitted, and the indicator is embedded directly into a cladding made of a polymer that is at least semi-permeable to the desired agent to be detected.

Figures 3, 4:
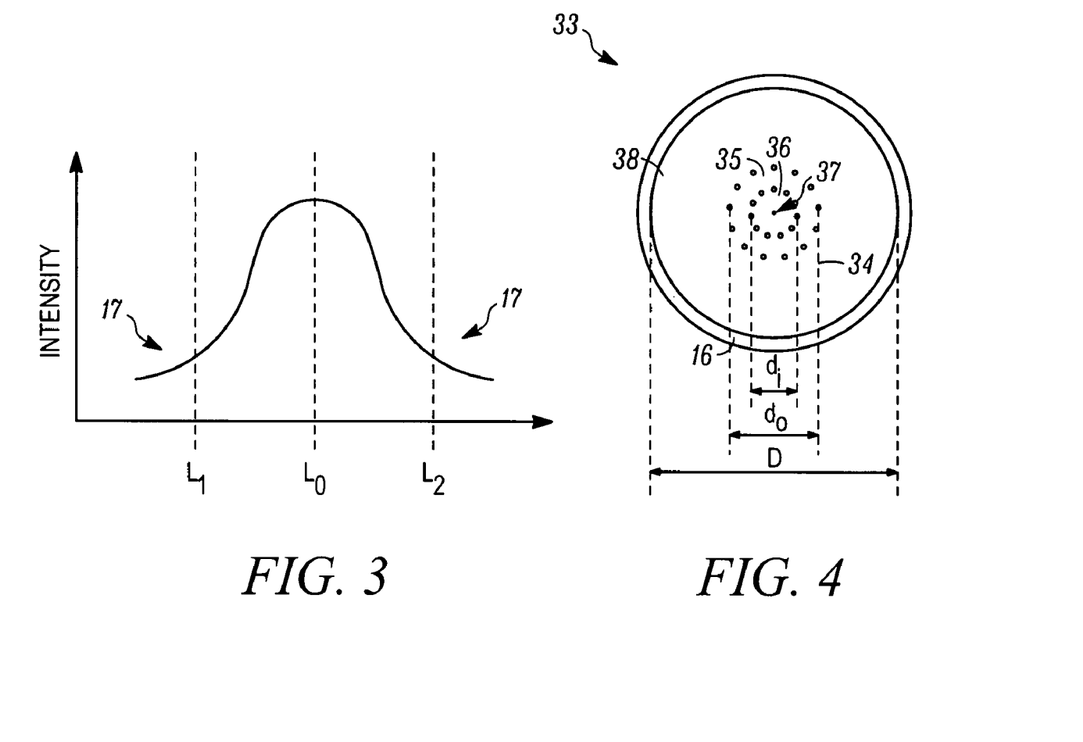
FIG. 3 is a mode field distribution useful in understanding the photonic crystal fiber shown in FIGS. 1 and 2.
FIG. 4 is a cross-sectional view of a photonic crystal fiber in accordance with another exemplary embodiment.

FIG. 3 is a mode field distribution useful in understanding the photonic crystal fiber 10 shown in FIGS. 1 and 2. Light propagating in the fiber 10 has an optical energy spatial distribution that is generally Gaussian shaped based on its intensity of light in relation to a distance from a central axis (B) of the photonic crystal fiber 10. For example, the spatial distribution of the light is generally at a maximum about the central axis (B) of the fiber 10 and decreases away from the central axis (B) in a Gaussian shape having evanescent tails 17. From the cross-sectional view of the photonic crystal fiber 10 shown in FIG. 2, a first position ($L_0$) corresponds to the central axis (B) and second and third positions ($L_1$ and $L_2$, respectively) approximate the interface between the cladding 14 and core 12 along the diameter of the photonic crystal fiber 10. The fiber 10 is structured to extend the evanescent tails 17 into the cladding 14 and can be structured such that the evanescent tails 17 extend into the polymer 16. For example, with the polymer 16 having a lower refractive index than the cladding 14 and the cladding 14 having a reduced thickness (e.g., in comparison with conventional single mode fibers), the evanescent tail 17 may be extended into the cladding 14 and/or the polymer 16.

In one embodiment, the photonic crystal fiber 10 may be structured such that a majority (e.g., about ninety percent (90%)) of the light intensity propagates along a central portion of the core 12 (e.g., between $L_0$ and $L_2$ and between $L_0$ and $L_1$), and a minority of the light intensity (e.g., about ten percent (10%)) is extended into the cladding 14 and the coating 16. The amount of the light intensity to be extended into the cladding 14 and the coating 16 may be varied (e.g., based on the refractive indices selected for the polymer 16, the cladding 14, and the thickness of the cladding 14).

Additionally, the photonic crystal fiber 10 may be structured to provide regions having different indices of refraction. For example, referring to FIG. 3, the photonic crystal fiber 33 utilizes the inner and outer claddings 36 and 38, respectively, to confine most of the spectral density along the solid glass annulus 35 for propagation through the photonic crystal fiber 33. In this embodiment, the outer cladding 38 extends the evanescent tail 17 into the polymer 16.

FIG. 4 is a cross-sectional view of a photonic crystal fiber 33 in accordance with another exemplary embodiment. In this embodiment, the fiber 33 has a glass member 34 coated with the indicator-embedded polymer 16 on the exterior of the glass member 34. A solid region (e.g., without holes) of the glass member 34 is oriented in the shape of an annulus 35 rather than along the central portion of the fiber 33. The annulus 35 has an outer diameter ($d_o$) that is a significant fraction of the diameter (D), or substantially similar to the diameter (D), of the glass member 34. A porous (e.g., having holes) inner cladding 36 is formed along the central portion of the fiber 33 (e.g., from an inner diameter ($d_i$) of the annulus 35 to a central axis 37 of the fiber 33), and a relatively thin porous outer cladding 38 is formed in a region extending beyond the outer diameter. The combination of the inner cladding 36 and the outer cladding 38 confines most of the light in a hoop-shaped mode within the annulus 35, although some of the evanescent field associated with this light extends into the polymer 16. With this embodiment, a single mode fiber of suitable thickness, strength, and light exposure to the polymer 16 may be constructed.

Figure 5:
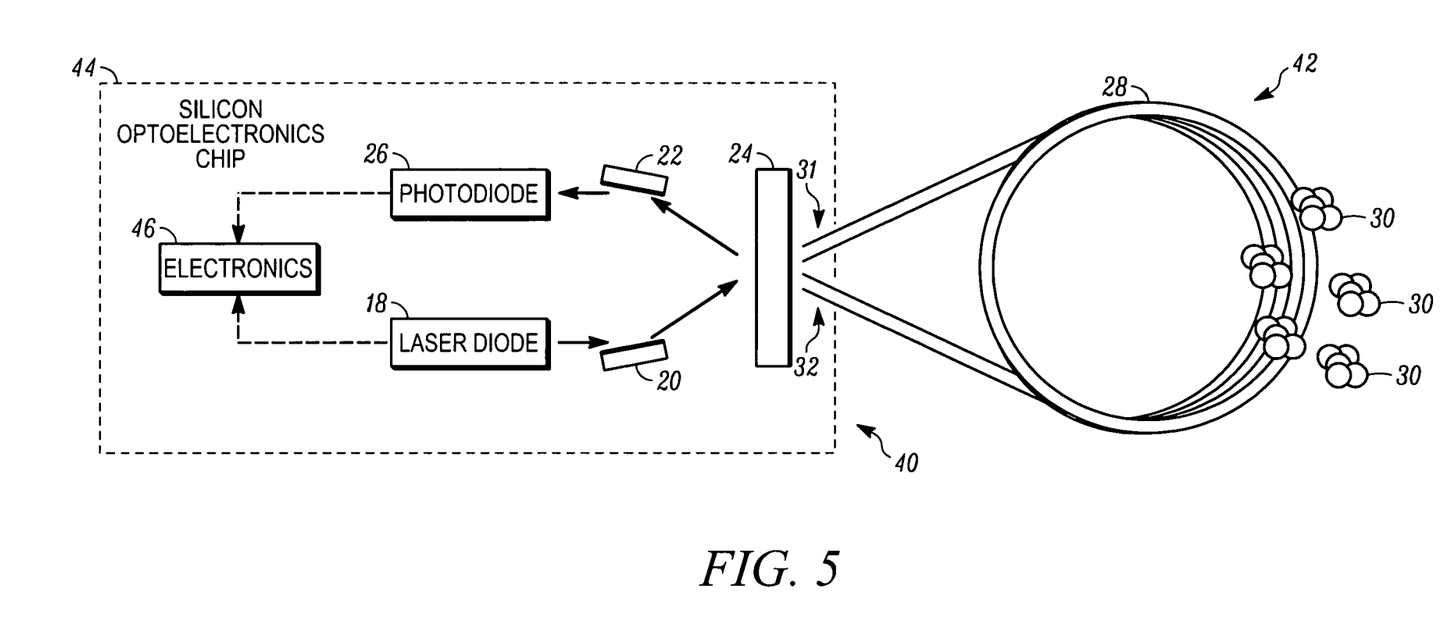
FIG. 5 is a schematic diagram of a chemical/biological agent sensor in accordance with an exemplary embodiment.

FIG. 5 is a schematic diagram of a chemical/biological agent sensor 40 in accordance with an exemplary embodiment. The sensor 40 comprises a tunable light source 18 (e.g., a laser diode), a first mirror reflector 20, a recirculator 24 (e.g., a highly reflective mirror with low, but non-zero transmittance), an optical fiber coil 28 having a first end 31 receiving light from the light source 18 via the first mirror reflector 20 and recirculator 24, a second mirror reflector 22 receiving a light output from a second end of the optical fiber coil 28 via the recirculator 24, a photodetector (e.g., a photodiode) 26, and an electronics module 46 coupled to the photodetector 26 and the light source 18. The recirculator 24 and optical fiber coil 28 together form a resonator 42. The resonator 42 may have a variety of configurations, such as a linear resonator, a ring resonator, or the like, and is described herein as in a ring resonator configuration. The light introduced to the resonator 42 is preferably monochromatic and circulates through multiple turns of the optical fiber coil 28 and for multiple passes through the coil via the recirculator 24. A light output from the resonator 42 is responsive to the absence and presence of a predetermined chemical/biological agent 30. The sensor 40 may additionally include a wireless transmitter (not shown) for transmitting detection data.

In an exemplary embodiment, the light source 18 is a tunable laser having frequency stability, a substantially narrow line width, and relatively high power capability. The light source 18 is tuned through a frequency region containing a frequency $f_0$ that corresponds with the resonance frequency in either a clockwise (CW) direction or a counter-clockwise (CCW) direction of light propagation through the optical fiber coil 28. In general, the recirculator 24 may be any optical element that reintroduces light emerging from one end of the optical fiber coil 28 into the other end of the fiber coil 28, thus causing light to propagate through the optical fiber coil 28 many times. The use of an input mirror instead of a fiber optic coupler for the recirculator 24 is one advantage of the sensor 40 since the mirror may be used to attenuate polarization errors and other error mechanisms, and may introduce fewer imperfections. However, the fiber coupler may function for the recirculator 24 is some applications.

The optical fiber coil 28 comprises a large mode, single mode, photonic crystal fiber (e.g., the photonic crystal fiber 10 shown in FIGS. 1 and 2 or the photonic crystal fiber 33 shown in FIG. 3) having a solid glass region and a relatively thin cladding surrounding the solid glass region, and a polymer coating the cladding. In one embodiment, the optical fiber coil 28 can be housed in a permeable package (not shown) for detecting the predetermined chemical/biological agent (e.g., associated with the indicator embedded in the optical fiber coil 28). An indicator is embedded in the polymer that reacts to a predetermined chemical/biological agent 30. The indicator may be a chemical or other substance that reacts to one or more chemical/biological substances (e.g., hydrogen sulfide, cyanide, chlorine, nerve agents, serin, and the like) and changes optical characteristics, for example color, optical loss, index of refraction, or the like.

With a solid glass core embodiment, a fiber having an extremely low bend loss is preferably used, and the optical fiber coil 28 preferably has a relatively large number of turns about a substantially small area. For example, the coil 28 may have from about 20-40 turns of the optical fiber about a one centimeter diameter. Generally, the longer the optical path, such as provided by the optical fiber coil 28, the greater the signal-to-noise ratio of the sensor 40. To improve the signal-to-noise ratio of the sensor 40, the optical path may be increased by increasing the number of turns of the optical fiber coil 28.

In operation, light produced by the light source 18 is directed to the first mirror reflector 20 which in turn directs this light to the recirculator 24. Light from the first mirror reflector 20 is scanned through the resonance frequency of the resonator 42 in a corresponding direction (e.g., the clockwise direction) of propagation, a first portion of which is transmitted through the recirculator 24 and into the first end 31 of the optical fiber coil 28. A second portion (i.e., a reflected wave) is reflected from the recirculator 24 to the second mirror reflector 22. The resonance frequencies for each of the CW and CCW paths through the optical fiber coil 28 are based on a constructive interference of successively circulated beams in each optical path within the resonator 42. After the first portion of light propagates through the core of the optical fiber coil 28, the light emerges from the second end 32 of the optical fiber coil 28. In this exemplary embodiment, the light emerging from the second end 32 is directed to the recirculator 24. A portion of this light is reflected back into the first end 31 by the recirculator 24 while another portion is transmitted (i.e., a transmitted wave) by the recirculator 24 to the second mirror reflector 22. The transmitted wave is a fraction of, and derived from, a recirculating light wave inside the resonator 42. The transmitted wave and the reflected wave are directed, via the second mirror reflector 22, to the photodetector 26 where these waves are interfered. As the frequency of the light is detuned away from the resonance, the transmitted wave becomes insignificant such that only the reflected portion impinges on the photodetector 26, indicating a maximum intensity with minimal to an absence of destructive interference. As the frequency of the light is scanned through the center of the resonance, the transmitted wave is maximized to produce a maximum destructive interference with the reflected wave, and thus provides a resonance lineshape having a minimum that is indicative of the resonance center.

To observe the resonance center of the resonator 42, in either the CW direction or CCW direction, the intensity at the photodetector 26 may be measured or a standard synchronous detection technique may be used. Applying a synchronous detection technique, the input light beam is sinusoidally phase-modulated, and therefore frequency modulated at a fundamental detection frequency ($f_m$), to dither the input beam frequency across the resonance lineshape as measured by the photodetector 26. For example, the electronic module 46 coupled to the photodetector 26 may demodulate the output of the photodetector 26 at $f_m$ to measure the resonance center indicated by the light output of the circulating light beam. At a line center of the resonance lineshape (e.g., indicating the resonance center), the photodetector 26 detects a minimum output at the fundamental detection frequency ($f_m$) and detects a maximum on either side of the resonance lineshape substantially where the slope of the resonance lineshape is greatest.

When the resonator 42 is off-resonance, an intensity signal maximum is observed, but the signal at $f_m$ is substantially zero. To observe the linewidth of the resonance lineshape, the light source 18 frequency is scanned such that the light intensity signal impinging on the photodetector 26 varies through at least a sequence of observing a half maximum, a minimum, and then another half-maximum, while the light source 18 frequency is scanned monotonically through resonance. Alternatively, another measure of the linewidth of the resonance lineshape may be obtained by monitoring a frequency difference between maxima of the demodulated signal at $f_m$ as the light source 18 frequency is scanned monotonically. In this case, a measurement of the frequency difference between maxima of the demodulated signal at $f_m$ (e.g., between points of highest slope) is proportional to linewidth of the resonance lineshape, and thus proportional to the loss of the resonator 42. A light source 18 frequency excursion from half-maximum to half-maximum (e.g., between points of highest slope) represents the linewidth of the resonance lineshape, which indicates a loss within the optical fiber coil 28, and hence, a measure of the presence of the chemical agent or chemical substance or biological substance. A widening of the linewidth of the resonance lineshape represents the presence of the chemical agent or subject substance.

The light source 18 frequency excursion is measured by recording a light source 18 frequency difference between the time that the photodetector 26 observes on half-maximum signal and the time the photodetector 26 observes the second half-maximum signal. The light source 18 frequency at each of those two points in time may be measured directly or indirectly. One example of a direct measurement involves beating the light source 18 frequency with another light source that is not being scanned and measuring a beat frequency difference between the two points in time. An example of an indirect measurement, which may be less expensive, is to pre-calibrate the light source 18 frequency with respect to an electrical signal input used to scan the light source 18. Using a laser for the light source 18, this electrical signal input may be a current drive signal that changes the injection current of the laser, a current drive signal to a thermo-electric cooler that changes the temperature of the laser, or a voltage drive signal to a piezoelectric transducer that changes the pathlength of the laser cavity to change the laser frequency. In these cases, a laser frequency shift with respect to the corresponding drive signal can be factory-calibrated, and a measured drive signal excursion indicates a frequency excursion during operation.

When $f_0$ is tuned away from the resonance frequency of the resonator 42 in the CW direction, for example, the energy from the CW beam does not enter the optical fiber and the light is reflected off the highly reflective mirror of the recirculator 24 to produce a maximum intensity at the photodetector 26. When $f_0$ is tuned at the resonance frequency of the resonator 42 in the CW direction, the CW beam enters the optical fiber coil 28, and the light striking the photodetector 26 has a minimum output thereby indicating the resonance center. Similarly, if light is injected in the CCW direction, the CCW beam enters the optical fiber coil 28 when the CCW beam is tuned to the resonance frequency of the resonator 42 in the CCW direction.

When the chemical/biological agent 30 is in the presence of the optical fiber coil 28, the indicator embedded in the polymer, used either as a cladding or a coating over the cladding, of the optical fiber coil 28 reacts (e.g., binds) with the chemical/biological agent 30 and alters the optical properties of the optical fiber coil 28. For example, the altered optical properties of the optical fiber coil 28 include, but are not necessarily limited to, a change in the index of refraction or an increase or decrease in the optical absorbance or loss of the optical fiber coil 28.

In an exemplary embodiment, the sensor 40 is constructed on a silicon-based micro-optical bench 44 that integrates electronics (e.g., the electronic module 46) and optics and provides an efficient and expedient interface between the two. Miniature optical components having a feature size of as little as 10 μm, such as the mirror reflectors 20, 22, and the recirculator 24, may be mounted on silicon surfaces to eliminate large bulk optics, even though the light wave may be traveling in free space. Some of these optical functions may also be embedded in waveguides residing in the silicon. In this exemplary embodiment, the light source 18 and related frequency tuning components and the photodetector 26 may also be mounted on the optical bench. The use of these techniques allows the fabrication of optics in or on a silicon platform and thus integrated with the electronics.

The light source 18 may be a compound structure having several components that are mounted or formed on the micro-optical bench 44. For example, the light source 18 may be an external cavity laser diode placed between two reflective surfaces that are either formed or placed on the substrate of the micro-optical bench 44. Additionally, frequency-selective intra-cavity elements may be formed or placed within the laser diode cavity to produce a single frequency laser, such as a grating or an etalon. Additionally, elements may be included with the light source 18 that are mounted or formed external to the laser cavity, to shape or collimate the laser beam, such as one or more lenses.

A modulator (e.g., a piezoelectric transducer) (not shown) may be coupled to the optical fiber coil 28 to modulate the pathlength of the light (e.g., sinusoidal modulation) circulating through the optical fiber coil 28 during resonance linewidth determination so that a synchronous detection technique may be used. For example, the input light beam produced by the light source 18 is scanned through the resonance frequency $f_0$ of the resonator 42, and the modulator sinusoidally modulates the pathlength of the light circulating through the optical fiber coil 28. In another exemplary embodiment, the modulator is omitted when the light source 18 has frequency modulation capabilities incorporated therewith. In another exemplary embodiment, the laser frequency is fixed, and both the frequency scanning and the modulation are implemented by the modulator. In the latter case, the resonator resonance frequency is scanned through the region of the laser frequency, which is equivalent in principle to scanning the laser frequency across a fixed resonance frequency of the resonator 42.

Figure 6:
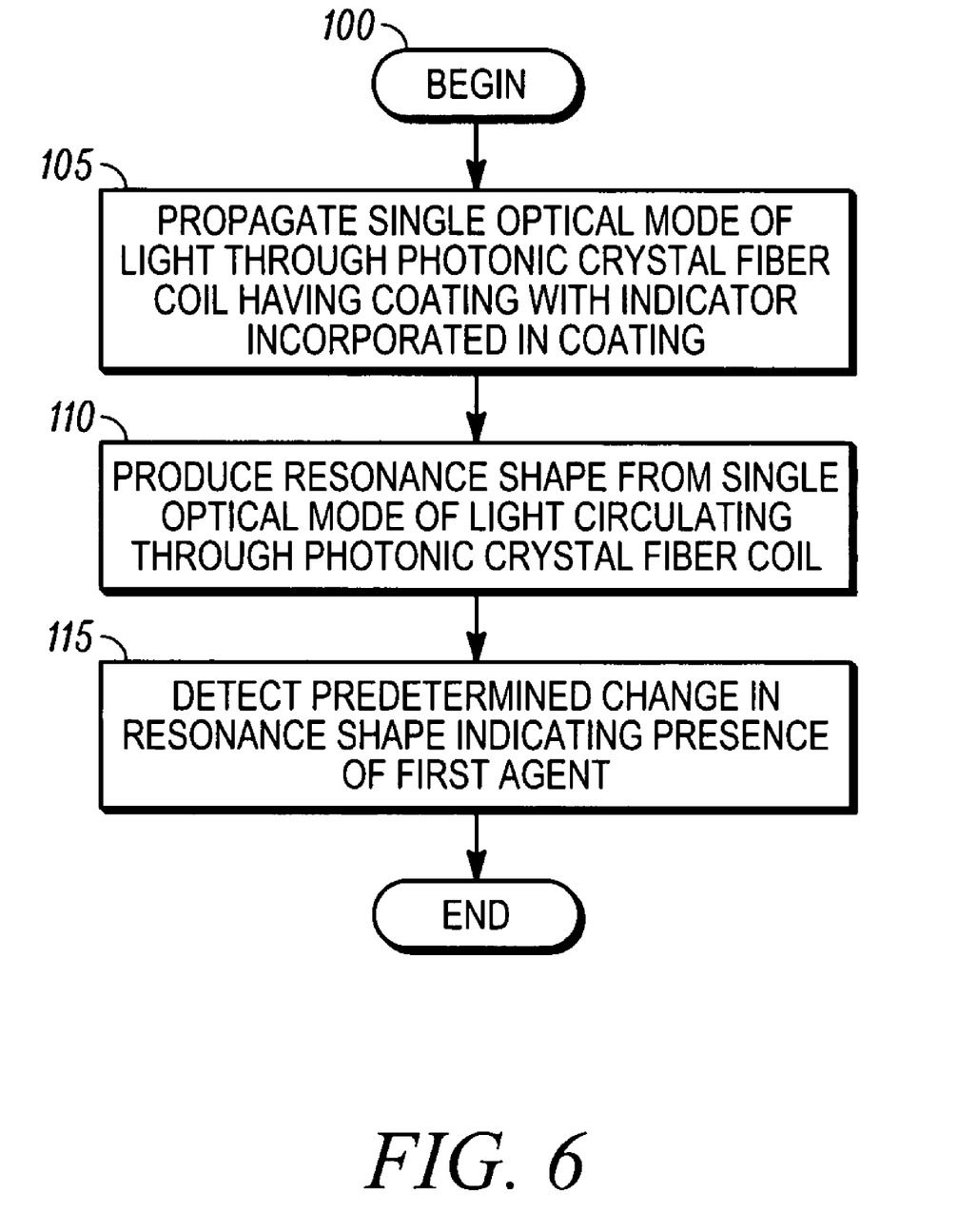
FIG. 6 is a flow diagram of a method for sensing one or more chemical/biological agents in an environment in accordance with an exemplary embodiment of the present invention.

FIG. 6 is a flow diagram of a method 100 for sensing one or more agents in an environment in accordance with another exemplary embodiment of the present invention. Referring to FIGS. 1-6, a single optical mode of a light beam is propagated through a photonic crystal fiber coil, as indicated at step 105. The photonic crystal fiber coil has a solid region, a cladding surrounding the solid region, and a polymer coating the cladding. An indicator is incorporated in the polymer. The indicator reacts with a predetermined agent (e.g., chemical/biological agent). For example, a light beam is propagated through the photonic crystal fiber 10 of the optical fiber coil 28, and the polymer 16 has an indicator embedded therein. In one exemplary embodiment, a single optical spatial mode of light has a Gaussian shape with a central portion (e.g., between $L_1$ and $L_2$), representing a majority of the intensity of the mode profile, and evanescent tails (e.g., evanescent tails 17) adjacent to the central portion. The photonic crystal fiber coil is configured to extend the evanescent tail of the mode through the cladding and into the polymer where the indicator is embedded. In one embodiment, the solid region of the photonic crystal fiber coil is a solid glass cylinder. For example, the photonic crystal fiber 33 comprises an annulus 35 having an outer diameter bordered by the outer cladding 38 and an inner diameter bordered by the inner cladding 36. In this embodiment, a majority of the mode of the light wave is propagated through this photonic crystal fiber coil along the solid glass cylinder, and the evanescent tail of the mode is extended from the solid glass cylinder through the first cladding and into the polymer.

A resonance shape is produced from the single optical mode of the light beam circulating through the photonic crystal fiber coil, as indicated at step 110. When determining the resonance lineshape from the light circulating in the optical fiber coil, the input light beam frequency is scanned across the resonance lineshape of the resonator containing the sensitive optical fiber coil. A predetermined change in the resonance shape is detected, as indicated at step 115. The predetermined change indicates a reaction of the indicator to the agent and may be a predetermined amount of energy loss, for example, represented as changes in the resonance lineshape.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. An apparatus for sensing an agent in an environment, the apparatus comprising:
 a resonator having a resonance frequency and comprising a photonic crystal fiber, the photonic crystal fiber comprising:
  a solid region configured to guide a substantially single optical mode of light, the substantially single optical mode having an evanescent tail;
  a first cladding surrounding an exterior of the solid region, the first cladding comprising a first periodic hole structure; and
  a polymer coating the first cladding, the polymer being at least partially porous having an embedded indicator, the first cladding and polymer together configured to extend a portion of the evanescent tail into the first cladding and the polymer;
 wherein the resonator is configured to produce a resonance shape centered at the resonance frequency, a predetermined change in the resonance shape indicating a reaction of the embedded indicator to the agent.

2. An apparatus according to claim 1, wherein the photonic crystal fiber comprises a glass region having a diameter greater than about 20 µm.

3. An apparatus according to claim 1, wherein the resonator has a finesse of greater than about 100.

4. An apparatus according to claim 1, wherein the photonic crystal fiber comprise a core in the solid region, and wherein the photonic crystal fiber is further configured to guide about 90% of the single optical mode through one of a group consisting of the core and a combined region comprising the core and the first cladding.

5. An apparatus according to claim 1, wherein the polymer has a refractive index, wherein the first cladding has a thickness and a refractive index greater than the refractive index of the polymer, and wherein the refractive indices of the polymer and the first cladding and the thickness of the cladding are selected to extend a portion of the evanescent tail through the first cladding and into the polymer.

6. An apparatus according to claim 1, wherein the solid region comprises a solid glass cylinder having an inner surface and an outer surface, the first cladding surrounding the outer surface, wherein the photonic crystal fiber further comprises a second cladding coating the inner surface, the second cladding comprises a second periodic hole structure.

7. An apparatus according to claim 6, wherein the first and second claddings are together configured to substantially confine a majority of a light wave within the solid glass cylinder and further configured to extend a portion of the evanescent tail through the first cladding and into the polymer.

8. An apparatus according to claim 6, wherein the photonic crystal fiber further comprises a glass member, the glass member having a diameter and comprising the solid glass cylinder, the first cladding, and the second cladding, and wherein the solid glass cylinder has an outer diameter, the outer diameter of the solid glass cylinder being a majority of the diameter of the glass member.

9. An apparatus according to claim 6, wherein the photonic crystal fiber is configured to guide about 90% of the single optical mode through the solid glass cylinder.

10. An apparatus for sensing an agent in an environment, the apparatus comprising:
- a tunable light source providing an input light;
- a resonator having a resonance frequency and comprising a coil, the coil comprising a photonic crystal fiber, the photonic crystal fiber comprising:
  - a solid region configured to guide a substantially single optical mode of light, the substantially single optical mode having an evanescent tail;
  - a first cladding surrounding the solid region and comprising a photonic crystalline structure; and
  - a polymer coating the first cladding, the polymer being at least partially porous and having an embedded indicator, the first cladding and the polymer together configured to extend a portion of the evanescent tail into the first cladding and the polymer;
- wherein the resonator produces a resonance shape centered at the resonance frequency as the tunable light source is tuned through a region about the resonance frequency, a predetermined change in at least one of the resonance shape and a free spectral range indicating a reaction of the embedded indicator to the agent.

11. An apparatus according to claim 10, wherein the resonator further comprises a optical coupler coupled to the coil, the optical coupler configured to receive the input light and further configured to transmit an output light from the coil, the output light indicating the resonance shape.

12. An apparatus according to claim 10, further comprising:
- a first reflector configured to receive the input light from the tunable light source and further configured to transmit the input light to the resonator;
- a second reflector configured to receive an output light from the resonator; and
- a photodetector configured to detect the resonance shape from the output light.

13. An apparatus according to claim 12, wherein the resonator further comprises an input mirror configured to receive the input light from the first reflector and further configured to direct a circulating light into the coil, the circulating light derived from the input light.

14. An apparatus according to claim 10, wherein the input light has a wavelength, and wherein the substantially single optical mode has a mode field diameter from about seven times (7×) to about thirty times (30×) the wavelength of the input light.

15. An apparatus according to claim 10, wherein the coil has a diameter of about 1 cm.

16. A method for sensing an agent in an environment, the method comprising the steps of:
- propagating a light wave in a single optical mode through a photonic crystal fiber coil, the photonic crystal fiber coil comprising a solid region, a cladding surrounding the solid region, and a polymer coating the cladding, the polymer having an indicator incorporated therein;
- producing a resonance shape from the single optical mode in which the light wave is propagating through the photonic crystal fiber coil; and
- detecting a predetermined change in the resonance shape, the predetermined change indicating a reaction of the indicator to the agent.

17. A method according to claim 16, wherein the step of detecting comprises detecting a predetermined change in the resonance shape, the predetermined change indicating the agent selected from a group consisting of chemical agents and biological agents.

18. A method according to claim 16, wherein the single optical mode has an evanescent tail, and wherein the step of propagating comprises extending the evanescent tail through the cladding and into the polymer.

19. A method according to claim 16, wherein the solid region comprises a solid glass cylinder, and wherein the step of propagating comprises propagating a majority of the single optical mode along the solid glass cylinder.

20. A method according to claim 19, the single optical mode comprises an evanescent tail, and wherein the step of propagating comprises extending the evanescent tail from the solid glass cylinder through the cladding and into the polymer.

* * * * *